United States Patent [19]

Kirschen

[11] 4,035,082

[45] July 12, 1977

[54] METHOD TO TEST FOR CHEMICALLY HARDENED GLASS LENSES

[75] Inventor: Morris Kirschen, Modesto, Calif.

[73] Assignee: Kirk Optical Lens Co., Inc., Farmingdale, N.Y.

[21] Appl. No.: 565,345

[22] Filed: Apr. 7, 1975

[51] Int. Cl.² ........................................... G01B 11/16
[52] U.S. Cl. ..................... 356/114; 356/33; 356/124
[58] Field of Search ................. 356/32, 33, 34, 35, 356/114, 124, 239

[56] References Cited

U.S. PATENT DOCUMENTS

| 3,586,444 | 6/1971 | Sproul et al. | 356/239 |
|---|---|---|---|
| 3,810,698 | 5/1974 | Alaska | 356/114 |
| 3,815,997 | 6/1974 | Alaska | 356/114 |
| 3,822,096 | 7/1974 | Wilms et al. | 356/124 |

OTHER PUBLICATIONS

Littman, G. "Chemical Hardening of Ophthalmic Lenses", *Manufacturing Optics International*, Oct. 1973, p. 489t.

Primary Examiner—John K. Corbin
Assistant Examiner—R. A. Rosenberger
Attorney, Agent, or Firm—Bauer, Amer & King

[57] ABSTRACT

A device to test for the presence of chemically hardened glass wherein a collimated light source and a windowed container are filled with a fluid of refractive index substantially equalling that of the glass. The glass is immersed in the container with the container placed between crossed polarizers. When the glass is chemically hardened, light traversing therethrough is refractively bent thereby to produce a component of the light vector in the optical axis of one of the polarizers and an observable light pattern emanating therefrom.

2 Claims, 4 Drawing Figures

U.S. Patent   July 12, 1977   4,035,082
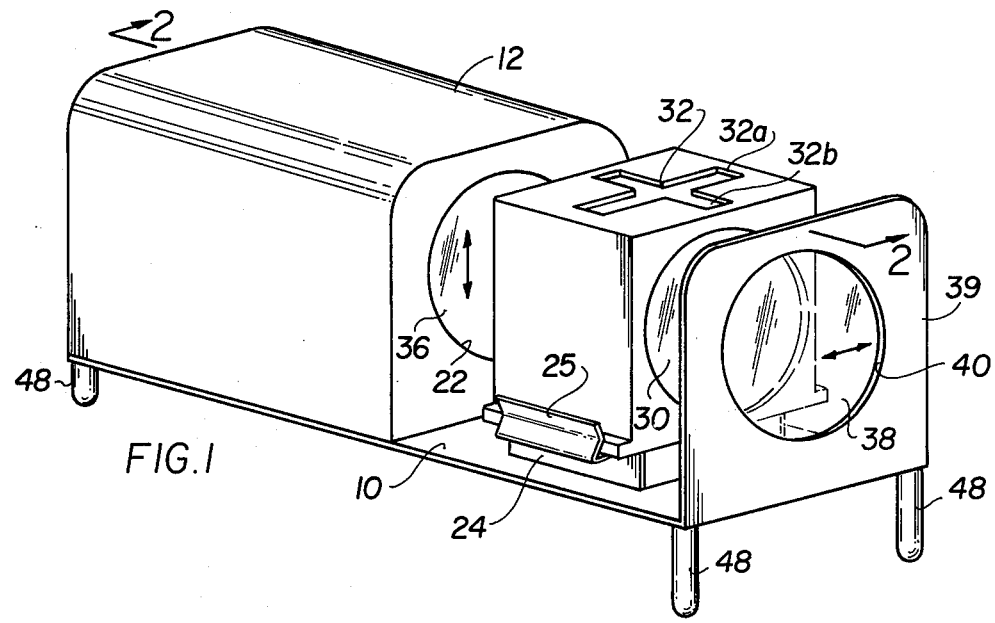
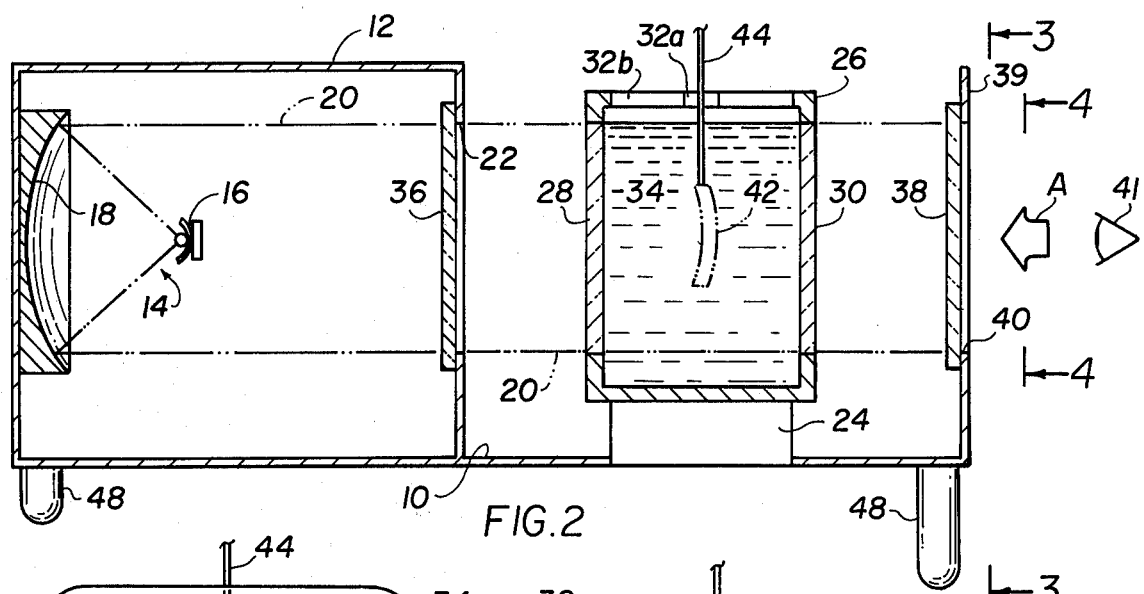
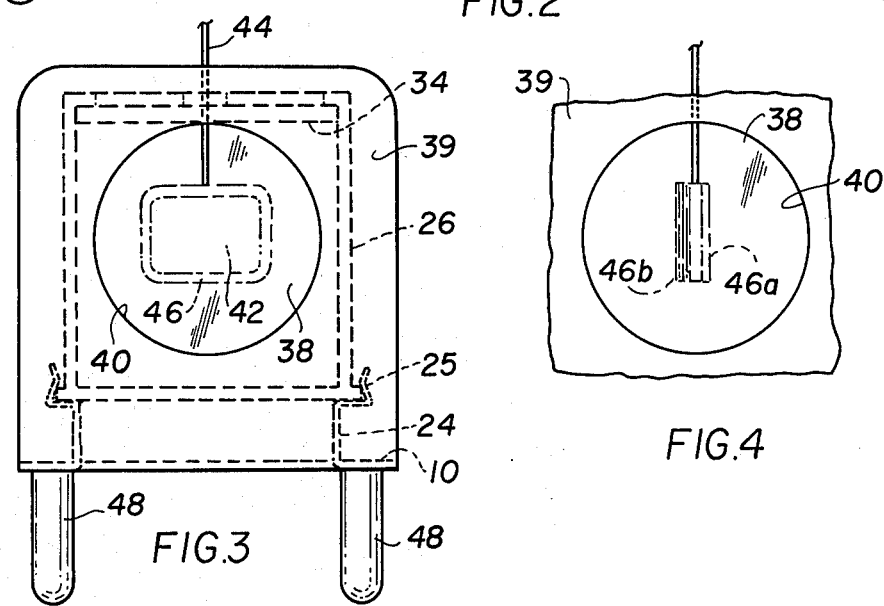

METHOD TO TEST FOR CHEMICALLY HARDENED GLASS LENSES

This invention relates to lens inspecting and more particularly the present invention relates to a method and apparatus to determine if a glass ophthalmic lens is chemically treated or hardened.

The necessity of glass lenses and particularly ophthalmic lenses to exhibit some degree of impact resistance is evident. Indeed, recent Federal Regulations of the Food and Drug Administration mandate all prescription ophthalmic lenses exhibit a prescribed level of impact resistance. Generally, it is the practice to harden the glass so that the same will then exhibit the required resistance. More specifically, the hardening or tempering can be effected by either or two procedures. One procedure employs a thermal hardening, the other employs a chemical hardening.

In the former procedure, the requisite hardness and impact resistance is induced by heating the glass to near its softening temperature after which the glass is "quenched" or rapidly cooled. The rapid rate of heat extraction severely strains the glass structure setting up a complex stress distribution through the lens. This stress distribution is defined by a perimetric boundary layer about the glass in biaxial compression and the remaining interior glass region in tension. In this prestressed configuration, the resulting strength is a composite of the inherent strength and the added strength induced by the hardening process.

In the latter chemical procedure, the glass lens is hardened by an ion exchange process that strains a perimetric boundary of the glass. More particularly, in the ion exchange technique a larger monovalent alkali metal such as potassium is deposited on the surface of the lens by exchange with the smaller monovalent alkali metal ion, sodium, comprising the glass. The potassium ion is larger than the sodium ion so that the ion exchange produces a densely packed surface or boundary layer which is characteristic of a compressive state. Hence the ion exchange results in a prestressed lens having a highly compressively stressed boundary region or layer and a tensilely stressed interior.

These two procedures are highly efficient so much so that neither of them can be ascertained by the naked eye. While nondetection is of importance to the wearer, if not the major reason for the widespread adoption of these procedures, knowledge of whether the glass has been hardened either chemically or thermally must be ascertained by those who work with or grind the glass. Determination of treated glass and the specific treatment is important because the procedures are different for hardened or treated glass and that glass which is untreated.

Several non-destructive testing techniques and apparatuses are extant to determine if the glass or lens has been treated and hardened by the heating and quenching approach. In the use of such apparatuses, the glass will exhibit a balanced stress pattern, usually in the form of a Maltese cross-shape when viewed after being placed between spaced and crossed polaroids. Yet, application of these conventional polariscopes to chemically treated lenses is unproductive since the outer ion layer is not of sufficient thickness to impart the requisite optical activity or refractive bending to effect a recognizable pattern. In the apparatus of U.S. Pat. No. 3,810,698, an expensive analyzer employing a complex arrangement of accurately machined parts is disclosed to reveal the presence of the ion boundary layer by use of prisms and polarizers. U.S. Pat. No. 3,746,450 relates to a device to test for, inter alia, chemically treated glass, but requires that the confronting radius of curvature for the surface wave transducer be at least as short as the shortest radius of curvature of the lens or lens portion to be examined. Further, the angle of incident light must be confined between predetermined extremes lest it fail to traverse the so-called wave guide structure.

It is, therefore, an object of the present invention to provide a simple, easily utilized, inexpensive device requiring no moving parts or technical skill to test whether glass has been hardened by chemical treatment.

It is another object of the present invention to provide a device to non-destructively test for the presence of a chemically induced hardening layer using a plane polariscope.

It is a further object of the present invention to provide a reliable non-destructive test for the existence of a chemically induced hardening layer by production of an optical pattern recognizable as such by the viewer.

It is still a further object of the present invention to provide an analyzer to determine the existence of a chemically deposited hardening layer on ophthalmic lenses that accepts a variety of lens sizes.

It is yet another object of the present invention to provide a reliable non-destructive test apparatus for chemically hardened glass that is adapted for use with a variety of lens sizes and shapes.

Other objects and features of the present invention will become apparent from the following detailed description considered in connection with the accompanying drawings. It is to be understood, however, that the drawings are designed for purposes of illustration only and not as a definition of the limits of the invention for which reference should be made to the appending claims.

In the drawings wherein the same reference numeral denotes the same element throughout the several views:

FIG. 1 is a perspective view of the testing device according to the teaching of the invention;

FIG. 2 is a sectional view taken along the lines 2—2 of FIG. 1 looking in the direction of the arrows;

FIG. 3 is an end view of the apparatus along lines 3—3 of FIG. 2 looking in direction of the arrows to reveal a light halo as seen by an observer and indicating the presence of a chemically deposited ion boundary with the test specimens broadside or perpendicular in the light beam; and FIG. 4 is a partial view of FIG. 2 looking along the lines 4—4 and enlarged for purposes of clarity and showing the fringe pattern observed when the specimen of FIG. 2 is orientated parallel in the light beam.

Referring now to the drawings and particularly FIGS. 1 through 3, there is shown the inventive apparatus including a stand or frame 10 having attached thereto a housing 12. A source of beam illuminating means, indicating generally be reference numeral 14, is situated in the housing as shown. By way of illustration only, means 14 is shown as a point source 16 operable to radiate only a cooperating parabolic reflecting surface 18 and thereby produce a collimated wave front or illumination beam 20. As used in this specification, reference to the source of illumination is meant to include illumination in the optical spectrum as well as the spectral domains of infrared and ultraviolet. Indeed, illumination by ultrasonic energy as well as radio frequency energy is within the scope of the inventive concept. Beam 20 exits housing 12 through as aperture 22 defined therein. Of course, illumination means 14 can assume various constructions, one such simple one being an incandescent light bulb. In a more sophisticated approach, means 14 might include a monochromatic light source such as a mercury vapor lamp or indeed a low powered laser. Further still, it is possible to use a solid state light source such as a light emitting diode (LED). As discussed below, the frequency of illuminating discharge of source 14 can range from infrared to ultraviolet.

A holder 24 is attached to and supported on frame 10. A container or immersion chamber 26 is detachably mounted on the holder 24 by spring clips 25 for removable support from the frame 10. Two opposed front and rear walls of container 26 are defined by confronting transparent windows 28 and 30 that fluid-tightly close their respective ends of the container 26. Holder 24 positions the container 26 and its windows so that the plane of the windows is perpendicular or broadside to the longitudinal axis of the light beam 20 radiating through aperture 22. It will be appreciated that aperture 22 is sized to illuminate the whole of the frontal area of windows 28 and 30.

The interior of container 26 is fluid tight, with the container further defined by an access cross slot array 32 on the top side thereof having broadside slot 32a and a slot 32b aligned with light beam 20. A fluid 34 having an index of refraction approximately equalling the refractive index of the glass to be tested is poured into and fluid-tightly held in the container.

A first plane polarizer 36 is positioned and held by any convenient means (not shown) inboard in housing 12 and broadside across the path of the collimated light beam 20. Customarily, the polarizing screen 36 is referred to as the "polarizer" and may have its axis of polarization or optical axis in any relative angular displacement. In the example shown, for ease of description this axis of polorization is arranged vertical so that the light 20 emanating from the leftward face of polarizer 36 and radiating from aperture or window 22 is vertically polarized before passing through front window 28. A second plane polarizer 38 is held positioned by any convenient means (not shown) broadside across that portion of collimated light beam 20 radiating through rear discharge window 30. For convenience the second polarizer 38, customarily referred to as the "analyzer", is supported in any convenient manner (not shown) on an upstanding portion 39 frame 10 formed with a viewing aperture 40. Analyzer 38 overlies window 40 and has its axis of polarization shifted or out of phase 90° relative to the polarization axis of first polarizer 36.

In the example shown, the polarization or optical axis of polarizer analyzer 38 would be horizontal since, as before noted, the optical axis of polarizer 36 was vertical. Of course, the vertical and horizontal orientation of respective polarizers 36 and 38 was for illustration only. Other angularities are available with the requirement being that axis of polarization between the two spaced polarizing screens be relatively shifted 90° or crossed with respect to each other. When the "polarizer" and analyzer are so crossed, a dark field will be observed on screen or analyzer 38 when viewed at 41 of FIG. 2 and looking in direction of the arrow A.

As plane polarizers, screens 36 and 38 are optical elements which absorb the components of the light vector not vibrating in the direction of the axis of polarization of the screen. Hence, when light passes through either plane polarizing screen 36 or 38, the optical element will absorb that component of the light vector that is perpendicular to the axis of polarization and transmits substantially only the parallel light component. Typically, the optical elements or polarizer and analyzer are H-type Polaroid sheets manufactured by the Polaroid Corporation, Cambridge, Massachusetts. These elements are sheets of polyvinyl alcohol that have been heated, stretched, bonded to a supporting sheet of cellulose acetate butyrate, and then stained with a liquid containing iodine.

In operation, a glass or ophthalmic lens 42 upon which the test is being conducted, is attached to a support 44. Then glass 42 is then placed into the container 26 and immersed in the fluid 34 so that it is nearly normal to collimated beam 20.

The technician or observer at 41 then views the glass lens 42 of FIG. 2 in the direction of the arrow A. Light radiating from aperture 22 and illuminating access window 28 is polarized in a first direction by polarizing screen 36. The light illuminates the specimen 42 suspended in the fluid 34. Collimated beam 20 then radiates through discharge window 30 and impinges on second polarizing screen 38 where it is polarized once again in a second direction crossed or shifted 90° relative to that orientation effected by polarizing screen 36.

If lens or glass 42 is chemically untreated and immersed in the fluid 34 which has a refractive index substantially that of the glass, the interface between the glass and fluid is unable to effect a refractive bending or directional change for the light striking the glass normal to its surface. Hence, when the lens 42 is not chemically treated or chemically hardened, the beam 20 passes through the lens and liquid interface unimpeded. The dark field on or radiating from screen 38 remains uninterrupted. However, if the glass lens 42 has been chemically treated or hardened as previously described, its boundary is defined by a dense ionic, although relatively thin layer or covering, conventionally of potassium ions. This ionic covering exhibits a different index of refraction than that of the lens or glass 42 and complementary refractive fluid 34.

When the chemically treated glass lens 42 is held broadside in slot 32a across polarized beam 20, the plane of the glass is for the most part normal to the light beam 20. The light striking the glass need only traverse the relatively thin ionic covering and glass under which condition the optical activity or bending afforded the ionic layer is minimal. Thus, most of the light again traverses the lens unimpeded or without significant bending. In consequence, the axis of polarization of analyzer or second screen 38 is able to effect a nearly complete light cancellation or blockage when viewed at 41 of FIG. 2 and as seen in FIG. 3. However, the lateral border of the glass 42 also carries an ionic covering. Light striking this lateral border and ionic covering will traverse an ionic layer of optical length equal to the thickness of the glass. This lateral border being as "thick" as the glass thickness is able to impart enough optical activity or refractive bending to the light traversing therethrough to disturb or scatter the complete polarizing effect of first polarizing screen 36. Hence, that amount of light which traverses the ionic covering of the lateral border is no longer totally polarized 90° out of phase or crossed with respect to polarizing screen 38. This light vector shifting or rotation results in some component of the vector being aligned along the axis of polarization of the screen 38 and radiates therethrough. A halo effect 46 is produced about and defining the lateral border or broadside edge region of the glass 42 when the same is orientated across beam 20. As seen in FIG. 3, the halo border 46 indicates positively the presence of a chemically hardened glass.

Of course, this birefringent effect or different refractive bending afforded by the ionic layer is proportional to the thickness of the layer as well as, inter alia, the refractive index thereof, the frequency of beam 20 and the thickness and curvature of lens 42. A more pronounced effect resulting from the presence of a chemically deposited hardening layer is seen in FIG. 4 which indicates the pattern observed when a viewer 41 looks along arrow A of FIG. 2. In FIG. 4, glass 42 of FIGS. 1 through 3 is rotated 90° and is lowered through slot 32b so as to be aligned along or with the axis of beam 20 instead of broadside across it. It is to be understood that the pattern shown is illustrative only, it being dependent on, for example, the curvature of the lens. Assuming that the right side of the lens is convex in profile and the "inside" or left side is concave, some of the light striking the right side will traverse the ionic boundary for an optical length nearly equal to the length of the lens. This will effect a significant refractive bending for light so doing and may even totally cancel the directional effects of first polarizing screen 36. Screen 38 will then have little attenuating effects on this light so that a bright halo 46a is observable through the screen 38. The brightness of band 46a may appear discontinuous, since light traversing through the rightward layer experiences differing scatter or bending depending on the "length" or thickness of the ionic layer it must traverse. This length or path distance of the incident ray through the ionic boundary depends, in part, on the height or spacing of the ray from the included interface of the boundary layer and lens, and the curvature of the lens.

For light incident on the left side of lens 42 and viewed edgewise as noted in FIG. 4, an array of bands 46b of differing intensity is seen. For light incident along this side of the lens, some rays will strike the glass, and depending on the severity of curvature of the glass, enter fluid 34 adjacent the glass and then once again re-enter the glass and ionic covering before exiting into fluid 34 and window 30. This optical path will significantly effect the vector orientation of the light and for some optical traverses may even totally cancel the effects of the first polarization afforded by screen 36. Therefore, some of the light incident on the left side of lens 42 will contain a component of the light vector in the optical axis or axis of polarization of screen 38 and pass therethrough unimpeded. This action produces a halo light array 46b radiating from screen 38.

Generally, the index of refraction of chemically hardened glass is so near that of ordinary cross glass which is 1.515, that a fluid of this refractive index is adequate for most test specimens. Although many fluids have a refractive index of substantially 1.515, one such fluid has been made of a mixture of mineral oils and polychlorinated biphenyls. The frame 10 may be conveniently supported on a shelf or other suitable surface by the lens 48 which may be adjustable by means not shown. Moveover, it is within the contemplation of the invention to rearrange the position of the screens 36 and 38 from that shown in the drawing and described to replace the windows 28 and 30.

The frequency of beam 20 may vary from infrared to ultraviolet, but at these extremes of the optical spectrum the attenuation of window means 28 and fluid 34 must be given consideration. Then, too, automatic means are available to sense the transmission of light through screen 38 to reveal the presence of a chemically hardened specimen. One such automatic means might comprise a photo transistor or photocell, the output of which drives an analog or digital transducer.

While only a single embodiment of the present invention has been shown, it is to be understood that many changes and modifications can be made hereto without departing from the spirit and scope hereof. It is the intention, therefore, to be limited only as indicated by the scope of the claims appended hereto.

What is claimed is:

1. A method to determine if a glass lens is chemically hardened including the steps of,
    immersing the glass lens to be tested in a fluid medium having a refractive index substantially that of the glass lens with the peripheral rim of the glass lens unobstructed and visible,
    placing the immersed glass lens between spaced crossed polarizers,
    and passing an illuminating beam serially through one of the polarizers, the immersed glass lens and then the other of the polarizers to produce a light halo perimetrically about the glass lens when the same has been chemically treated.
2. The method of claim 1, the illuminating beam being in the optical spectrum.

* * * * *